United States Patent [19]

Ken

[11] Patent Number: 5,582,619
[45] Date of Patent: Dec. 10, 1996

[54] STRETCH RESISTANT VASO-OCCLUSIVE COILS

[75] Inventor: Christopher G. M. Ken, San Mateo, Calif.

[73] Assignee: Target Therapeutics, Inc., Fremont, Calif.

[21] Appl. No.: 497,331

[22] Filed: Jun. 30, 1995

[51] Int. Cl.⁶ ................................. A61M 29/00
[52] U.S. Cl. .................. 606/191; 606/108; 606/198; 623/1
[58] Field of Search .................... 606/151, 213, 606/191, 108, 157, 158, 194, 195; 623/1, 12, 53, 164

[56] References Cited

U.S. PATENT DOCUMENTS

| | | |
|---|---|---|
| 3,174,851 | 3/1965 | Buehler et al. . |
| 3,351,463 | 11/1967 | Rozner et al. . |
| 3,753,700 | 8/1973 | Harrison et al. . |
| 4,994,069 | 2/1991 | Ritchart et al. . |
| 5,122,136 | 6/1992 | Guglielmi et al. . |
| 5,217,484 | 6/1993 | Marks . |
| 5,226,911 | 7/1993 | Chee et al. . |
| 5,234,437 | 8/1993 | Sepetka . |
| 5,250,071 | 10/1993 | Palermo . |
| 5,261,916 | 11/1993 | Engelson ................... 606/108 |
| 5,304,194 | 4/1994 | Chee et al. . |
| 5,304,195 | 4/1994 | Twyford, Jr. et al. ............ 606/191 |
| 5,312,415 | 5/1994 | Palermo . |
| 5,350,397 | 9/1994 | Palermo et al. ............ 606/191 |
| 5,354,295 | 10/1994 | Guglielmi et al. ............ 606/191 |
| 5,365,942 | 11/1994 | Shank . |
| 5,382,259 | 1/1995 | Phelps et al. ............ 606/151 |
| 5,382,260 | 1/1995 | Dormandy, Jr. et al. ............ 606/151 |
| 5,387,219 | 2/1995 | Rappe . |

*Primary Examiner*—Michael Powell Buiz
*Assistant Examiner*—Kevin Truong
*Attorney, Agent, or Firm*—Morrison & Foerster

[57] ABSTRACT

This invention is an implantable vaso-occlusive device. It is typically a vaso-occlusive coil comprised of a primary helically wound coil which is then wound into a secondary shape. Central to the invention is the use of a stretch-resisting member fixedly attached within at least a portion of the primary coil. This stretch-resisting member is for the primary purpose of preventing stretching of the coil during movement of the coil e.g., by retrieval or repositioning after deployment. The device typically has a self-forming secondary shape made from a pre-formed primary linear helically wound, although it need not have the secondary form. Fibers may be introduced onto the device and affixed to the pre-formed linear member. The constituent member may be also be covered with a fibrous braid. The device is typically introduced through a catheter. The device is passed axially through the catheter sheath and assumes its form upon exiting the catheter without further action.

13 Claims, 5 Drawing Sheets

STRETCH RESISTANT VASO-OCCLUSIVE COILS

FIELD OF THE INVENTION

This invention is an implantable vaso-occlusive device. It is typically a vaso-occlusive coil comprised of a primary helically wound coil which is then wound into a secondary shape. Central to the invention is the use of a stretch-resisting member fixedly attached within at least a portion of the primary coil. This stretch-resisting member is for the primary purpose of preventing stretching of the coil during movement of the coil e.g., by retrieval or repositioning after deployment. The device typically has a self-forming secondary shape made from a pre-formed primary linear helically wound coil, although it need not have the secondary form. Fibers may be introduced onto the device and affixed to the pre-formed linear member. The constituent member may be also be covered with a fibrous braid. The device is typically introduced into the body through a catheter. The device is passed axially through the catheter sheath and assumes its secondary form upon exiting the catheter.

BACKGROUND OF THE INVENTION

Vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings which may be dimensioned to engage the walls of the vessels. Other less stiff helically coiled devices have been described, as well as those involving woven braids.

For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (by its passage through the catheter) and the coil assumes a relaxed configuration—which is better suited to occlude the vessel—once the device is so placed. Ritchart et al. describes a variety of shapes. The secondary shapes of the disclosed coils include "flower" shapes and double vortices. A random shape is described, as well.

Vaso-occlusive coils having attached fibrous elements in a variety of secondary shapes are shown in U.S. Pat. No. 5,304,194, to Chee et al. Chee et al. describes a helically wound device having a secondary shape in which the fibrous elements extend in a sinusoidal fashion down the length of the coil. These coils, as with Ritchart et al., are produced in such a way that they will pass through the lumen of a catheter in a generally straight configuration and, when released from the catheter, form a relaxed or folded shape in the lumen or cavity chosen within the human body. The fibrous elements shown in Chee et al. enhance the ability of the coil to fill space within the vasculature and to facilitate formation of embolus and subsequent allied tissue.

There are a variety of ways of discharging shaped coils and linear coils into the human vasculature. In addition to those patents which apparently describe only the physical pushing of a coil out into the vasculature (e.g., Ritchart et al.), there are a number of other ways to release the coil at a specifically chosen time and site. U.S. Pat. No. 5,354,295 and its parent, U.S. Pat. No. 5,122,136 both to Guglielmi et al., describe an electrolytically detachable embolic device.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195 to Twyford et al., shows a pusher-vaso-occlusive coil assembly having an affixed, proximally extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

Vaso-occlusive coils having little or no inherent secondary shape have also been described For instance, in U.S. patent application Ser. No. 07/978,320, filed pending Nov. 18, 1992, entitled "Ultrasoft Embolization Coils with Fluid-Like Properties" by Berenstein et al., is found a coil having little or no shape after introduction into the vascular space.

None of these devices are helical coils which contain a stretch-resisting member contained therein.

SUMMARY OF THE INVENTION

This invention is a vaso-occlusive device comprising a helically wound coil which is formed by winding a wire into a first or primary helix to form an outer helical member having first and second ends. A stretch resistant member is fixedly attached to at least one of the ends within the lumen of the coil.

The primary helix, with its included stretch-resistant member, may then be wound into a secondary form. The secondary form may be one which, when ejected from a delivery catheter, forms a specific shape. Such a shape might, e.g., fill a vascular cavity such as an aneurysm, or perhaps, a fistula. The stiffness of the various parts of the coil may be tailored to enhance the utility of the device for specific applications. Fibrous materials may be woven into the member or tied or wrapped onto it.

The device is used simply by temporarily straightening the device and introducing it into a suitable catheter, the catheter already having been situated so that its distal opening is at the selected site in the body. The device is then pushed through the catheter and, upon its ejection from the distal end of the catheter into the vascular cavity, assumes its relaxed or secondary shape.

The device is typically used in the human vasculature to form emboli but may be used at any site in the human body where an occlusion such as one produced by the inventive device is needed.

DESCRIPTION OF THE INVENTION

Figure 1:
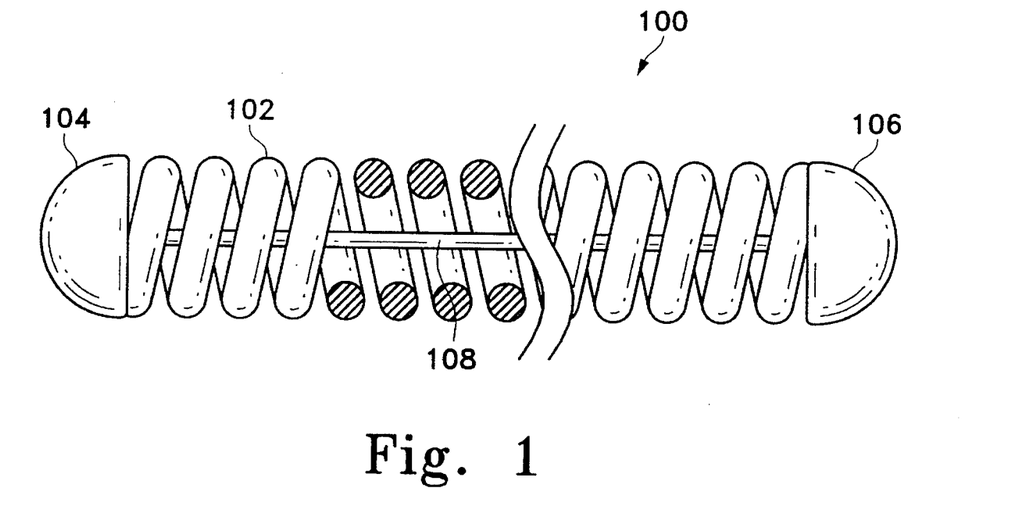
FIG. 1 shows a side view, partial cutaway of a vaso-occlusive coil made according to the invention having a generally linear wire stretch-resisting member.

FIG. 1 shows a side-view partial cross-section (or cutaway) of one highly desirable variation of the inventive coil (100). The variation shown in FIG. 1 is made up of a helically wound outer coil (102) having a first end (104) and a second end (106). I refer to this as the as the "primary" winding or shape. This variation includes a stretch-resisting member (108) which is fixedly attached both to the first end (104) and to the second end (106). In certain circumstances, it may be desirable to attach the stretch-resisting member (108) only to one of the two ends. The stretch-resisting member (108) in this variation is a simple wire which is soldered, brazed, glued or otherwise fixedly attached to the first end (104) or second end (106).

The material used in constructing the vaso-occlusive coil (102) and the stretch-resisting member (108) may be any of a wide variety of materials; preferably, a radio-opaque material such as a metal or a polymer is used. Suitable metals and alloys for the wire making up the primary coil (102) and the stretch-resisting member (108) include the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biologically inert. Highly preferred is a platinum/tungsten alloy, e.g., 8% tungsten and the remainder platinum.

The wire may also be of any of a wide variety of stainless steels if some sacrifice of radiopacity and flexibility may be tolerated. Very desirable materials of construction, from a mechanical point of view, are materials which maintain their shape despite being subjected to high stress. Certain "superelastic alloys" include nickel/titanium alloys (48–58 atomic % nickel and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing without deformation even when used as very small diameter wire.

If a superelastic alloy such as nitinol is used in the device, the diameter of the coil wire may be significantly smaller than that used when the relatively more ductile platinum or platinum/tungsten alloy is used as the material of construction.

The coils may be made of radiolucent fibers or polymers (or metallic threads coated with radiolucent or radiopaque fibers) such as Dacron (polyester), polyglycolic acid, polylactic acid, fluoropolymers (polytetrafluoro-ethylene), Nylon (polyamide), or even silk. Should a polymer be used as the major component of the vaso-occlusive member, it is desirably filled with some amount of a known radiopaque material such as powdered tantalum, powdered tungsten, bismuth oxide, barium sulfate, and the like.

The coil material is first wound into a primary coil (102). The primary coil is typically linear after it has been wound and annealed. Generally speaking, when the device (100) is formed of a metallic coil and that coil is a platinum alloy or a superelastic alloy such as nitinol, the diameter of the wire used in the production of the coil (102) and of the stretch-resisting member (108) will be in the range of 0.00025 and 0.006 inches. The wire of such diameter is wound into a primary coil (102) having a primary diameter of between 0.003 and 0.025 inches. For most neurovascular indications, the preferable primary coil (102) diameter is 0.008 to 0.018 inches. We have generally found that the coil wire may be of sufficient diameter to provide a hoop strength to the resulting device sufficient to hold the device in place within the chosen body site, lumen or cavity, without substantially distending the wall of the site and without moving from the site as a result of the repetitive fluid pulsing found in the vascular system.

The axial length of the primary coil will usually fall in the range of 0.5 to 100 cm, more usually 2.0 to 40 cm. Depending upon usage, the coil may well have 10–75 turns per centimeter, preferably 10–40 turns per centimeter. All of the dimensions here are provided only as guidelines and are not critical to the invention. However, only dimensions suitable for use in occluding sites within the human body are included in the scope of this invention.

Once the primary coil (102) is wound, the stretch-resisting member (108) is inserted into the lumen of the primary coil (102) and secured to the ends (104, 106), as desired.

Figure 2:
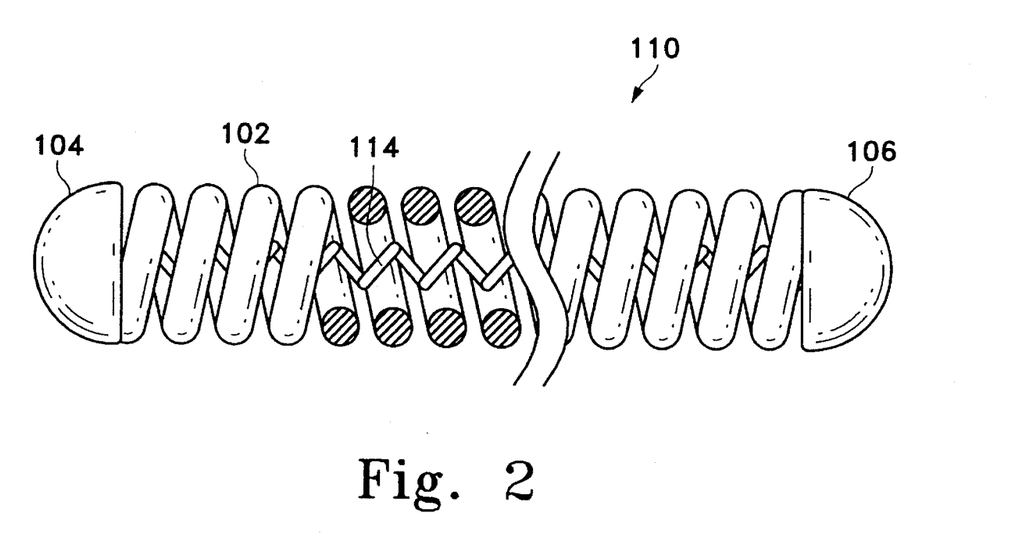
FIG. 2 shows a side view, partial cutaway of a vaso-occlusive coil made according to the invention having a generally helical stretch-resisting member.

FIG. 2 shows a side-view partial cross-section (or cutaway) of another highly desirable variation of the inventive coil (110). The variation shown in FIG. 2 is also made up of a helically wound outer coil (102) having a first end (104) and a second end (106). This variation includes a stretch-resisting member (114) which is fixedly attached both to the first end (104) and to the second end (106). The stretch-resisting member (114) in this variation is a helically wound coil which is soldered, brazed, glued or otherwise fixedly attached to the first end (104) or second end (106).

The stretch-resisting member (114) in this configuration provides a greater measure of lateral flexibility than the wire variation (108 in FIG. 1). It may be wound in either the same direction as is the outer coil (102) or in the alternate direction. A modest drawback to this variation is that it will stretch more than the FIG. 1 variation when axially stressed.

The variations shown in FIGS. 1 and 2 are designed to be deployed by use of a pusher and a catheter in the manner discussed in Ritchart et al, discussed above. Other methods (and concomitant fixtures or joints to accomplish those methods) may also be used.

Figure 3:
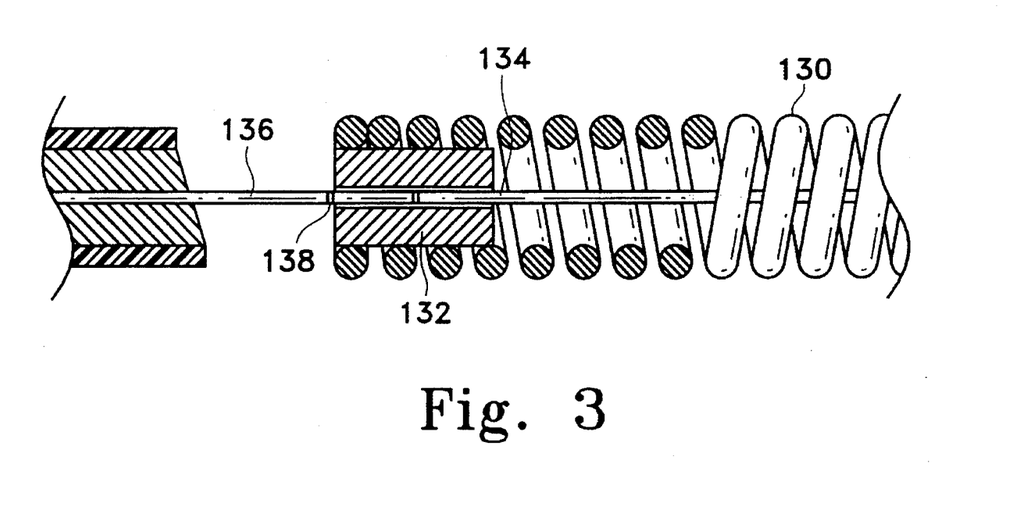
FIG. 3 shows a side view, partial cutaway of an electrolytically severable joint in combination with a vaso-occlusive coil made according to the invention.

For instance, the end of the device may be adapted to accept an electrolytically severable joint in the manner discussed in U.S. Pat. No. 5,354,295 and its parent, U.S. Pat. No. 5,122,136, both to Guglielmi et al., describe above. FIG. 3 depicts, in partial cross section, such a variation. The vaso-occlusive coil (130) is attached to a crimped end (132). The crimped end (132) is, in turn, crimped onto both the stretch resistant member (134) and the core wire (136). The core wire (136) is insulated, typically with a combination of polytetrafluoroethylene and parylene, except for a small sacrificial joint (138) which is intended to be the site of the electrolysis as the joint (138) is eroded or severed and the coil deployed into the body site. The details of this variation (sans stretch-resistant member (136)) are discussed in Gia et al, U.S. patent application Ser. No. 08/367,061, filed Dec. 30, 1994, the entirety of which is incorporated by reference.

Figure 4:
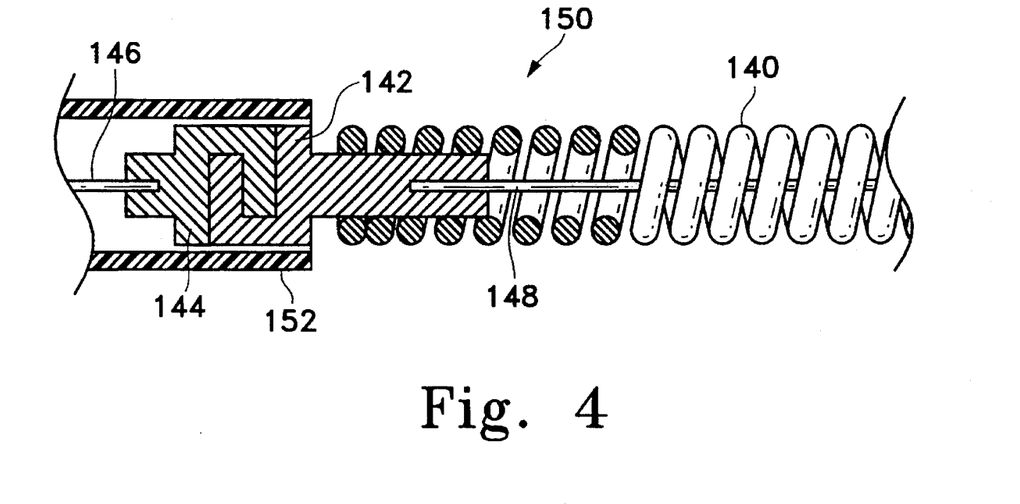
FIG. 4 shows a side view, partial cutaway of a typical mechanically detachable joint in combination with a vaso-occlusive coil made according to the invention.

FIG. 4 shows still another variation of a joint for releasing the inventive coil into a site within the human body. In this instance, the joint is mechanically deployed. The primary coil (140) incorporates interlocking clasps, one (142) located on an end of the coil (140) and one (144) located on the end of a pusher (146). The stretch-resisting member (148) is attached to the interlocking clasp (142). The coil assembly (150), made up of the primary coil (140), interlocking clasp (142), and stretch-resisting member (148) is deployed by retracting catheter body (or sheath) (152). Other mechanically deployable joints suitable for use with the inventive coil are described in:

U.S. Pat. No. 5,234,437, to Sepetka, (shows a method of unscrewing a helically wound coil from a pusher having interlocking surfaces)

U.S. Pat. No. 5,250,071, to Palermo, (shows an embolic coil assembly using interlocking clasps mounted both on the pusher and on the embolic coil)

U.S. Pat. No. 5,261,916, to Engelson, (shows a detachable pusher/vaso-occlusive coil assembly having an interlocking ball and keyway-type coupling)

U.S. Pat. No. 5,304,195, to Twyford et al. (shows a pusher-vaso-occlusive coil assembly having an affixed, proximally extending wire carrying a ball on its proximal end and a pusher having a similar end, which two ends are interlocked and disengage when expelled from the distal tip of the catheter)

U.S. Pat. No. 5,312,415, to Palermo (also shows a method for discharging numerous coils from a single pusher by use of a guidewire which has a section capable of interconnecting with the interior of the helically wound coil).

U.S. Pat. No. 5,350,397, to Palermo et al. (shows a pusher having a throat at its distal end and a pusher through its axis. The pusher sheath will hold onto the end of an embolic coil and will then be released upon pushing the axially placed pusher wire against the member found on the proximal end of the vaso-occlusive coil).

The entirety of which are incorporated by notice.

Figures 5, 6:
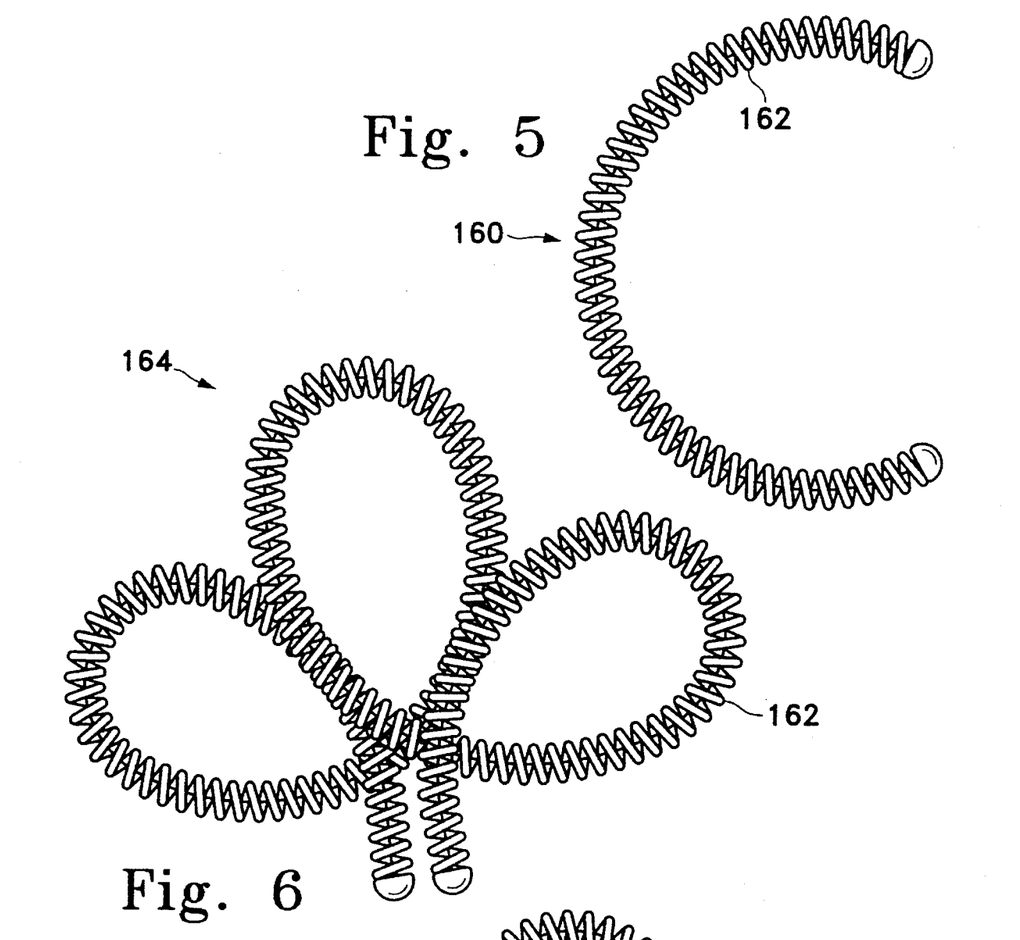
FIG. 5 shows a "C" shaped secondary shape for the inventive vaso-occlusive device.
FIG. 6 shows a clover-leaf secondary shape for the inventive vaso-occlusive device.
Figure 7:
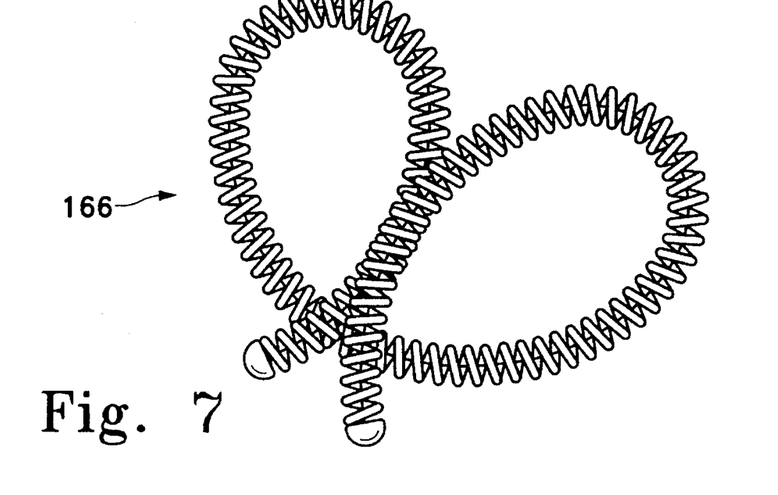
FIG. 7 shows a secondary shape for the inventive vaso-occlusive device.

As was noted above, the devices of this invention may have the simple linear shape shown in FIGS. 1 and 2 or may have shapes which are not so simple. FIGS. 5, 6, and 7 show what I term "secondary" shapes in that they are formed from the primary coil by the simple act of winding the primary coil on a form of a desired shape and then heat treating the so-formed shape. FIG. 5 shows a "C" shaped coil assembly (160) having a stretch-resistant member. (162). FIG. 6 shows a clover-leaf shaped coil assembly (164) also having a stretch-resistant member (162). FIG. 7 shows a double-loop coil assembly (166). These are indicative of the various secondary shapes suitable for this invention.

Figure 8:
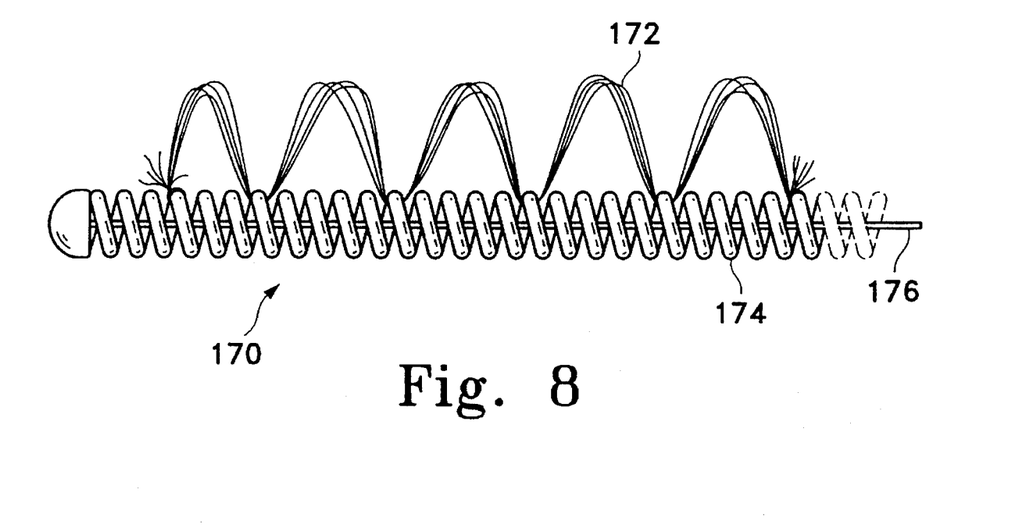
FIG. 8 shows attachment of fibrous material to the inventive vaso-occlusive device.

Additionally, these inventive devices may also be used in conjunction with various fiber adjuncts. FIG. 8 shows a partial side-view of a linear variation of the inventive device (170) having filamentary material (172) looping through the coil (174). This method of attachment is described in greater detail in U.S. Pat. Nos. 5,226,911 and 5,304,194, to Chee et al, the entirety of which are incorporated by reference. A further description of a desirable fiber attachment is shown in U.S. patent application Ser. No. 08/265,188, to Mirigian et al, filed Jun. 24, 1994.

Figure 9:
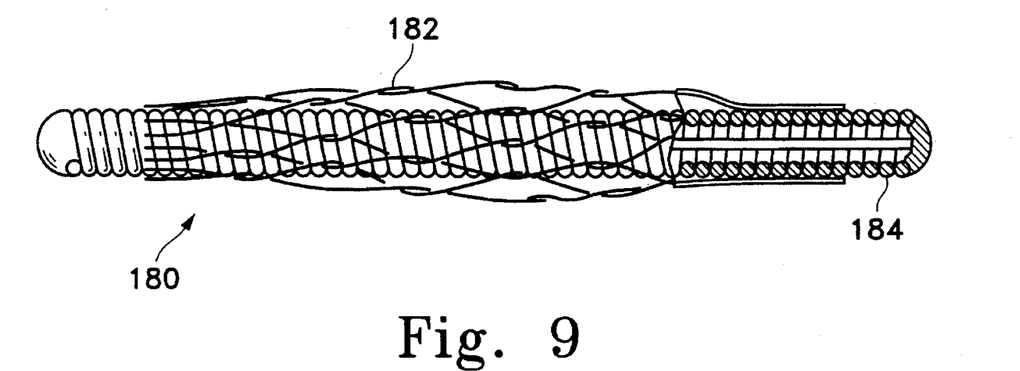
FIG. 9 shows attachment of braided fibrous material the inventive vaso-occlusive device.

FIG. 9 shows a partial cutaway of a device (180) having a braided covering (182) of a filamentary material and a stretch-resisting member (184). This method of enveloping a coil is described in greater detail in U.S. Pat. No. 5,382,259, to Phelps et al, the entirety of which is incorporated by reference.

The fibrous woven or braided tubular materials may be made from a biocompatible materials such as Dacron (polyester), polyglycolic acid, polylactic acid, fluoropolymers (polytetrafluoroethylene), Nylon (polyamide), or silk. The strands forming the braid should be reasonably heavy, e.g., having tensile strength of greater than about 0.15 pounds. The materials mentioned, to the extent that they are thermoplastics, may be melted or fused to the coils. Alternatively, they may be glued or otherwise fastened to the coils. Preferred materials are Dacron.

Figures 10A, 10B:
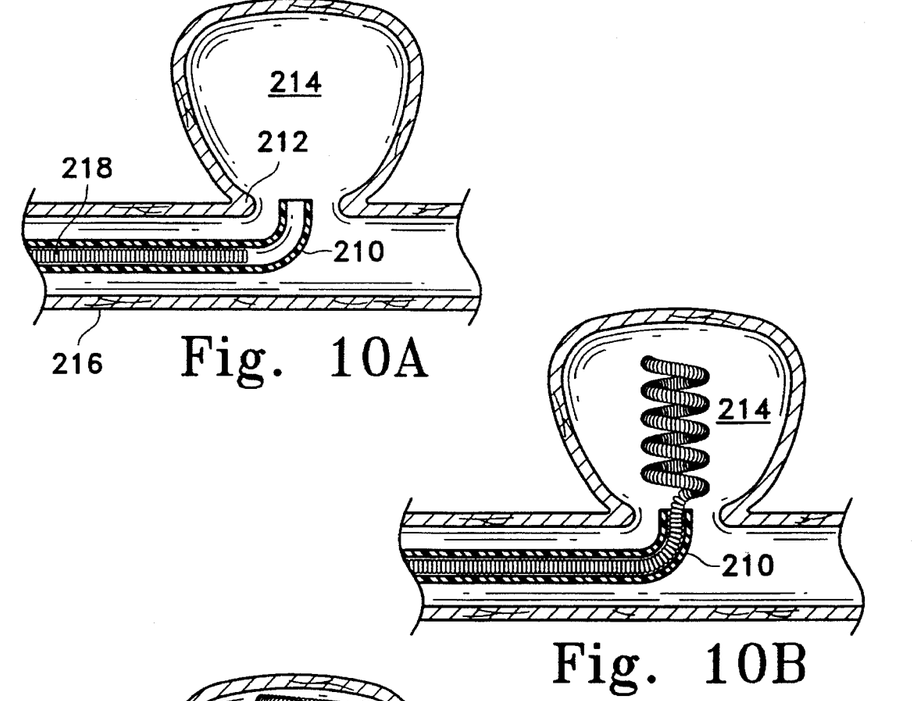
FIG. 10 shows a procedure for introducing a vaso-occlusive coil such as in FIGS. 1–4 into an aneurysm.
Figures 10C, 10D:
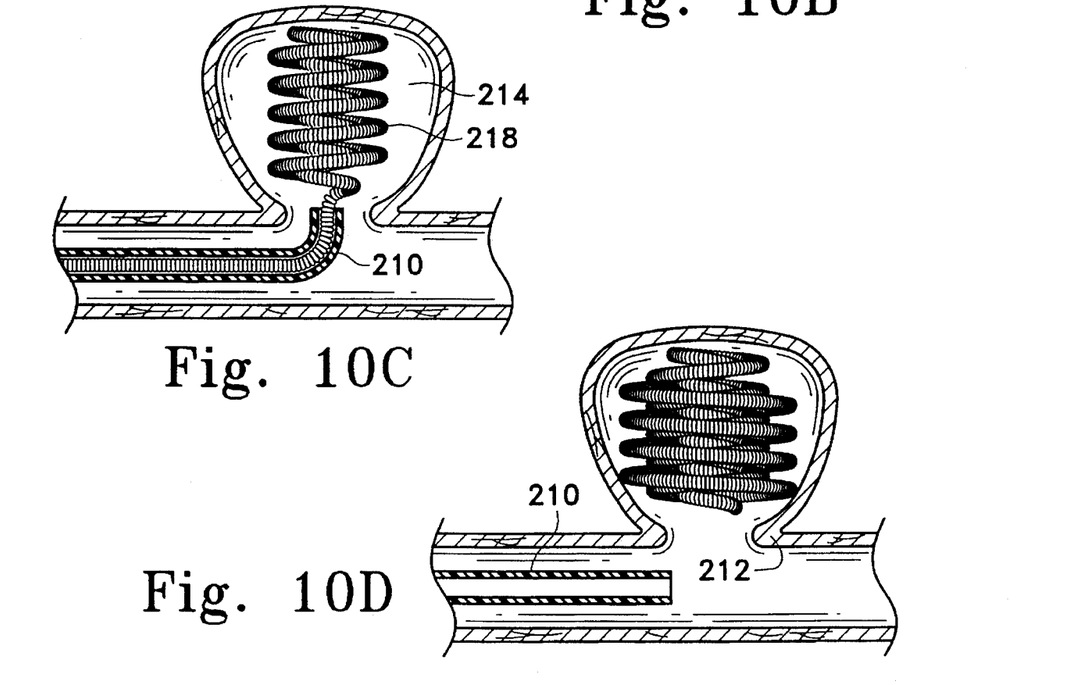

FIG. 10 depicts a common deployment method for introduction of the inventive vaso-occlusive devices described here. It may be observed that these procedures are not significantly different than those described in the Ritchart et al. patent mentioned above. Specifically, Step 1 shows the distal tip of a delivery catheter (210) which is within the opening (212) of an aneurysm (214) found in an artery (216). The distal or end section of the vaso-occlusive device (218) is shown within the catheter (210). In Step 2, the distal end portion of the vaso-occlusive device (218) has exited the distal end of the catheter (210) and has wound into a secondary shape within the aneurysm (214). Step 3 shows the completion of the formation of the secondary shape within the aneurysm (214). Step 4 shows the separation of the vaso-occlusive device (218) from the pusher, placement within the aneurysm (214), and the withdrawal of the catheter from the mouth of the aneurysm.

Once the inventive coil is in place in an aneurysm or other site, there may be an occasion during which the coil must be moved or even withdrawn. For instance, in step 4 of FIG. 10, the coil might extend through the mouth (212) of the aneurysm into the artery. Occlusion would not be desirable in the artery. A device such as the endovascular snare shown in U.S. Pat. No. 5,387,219, to Rappe, may then be used to grasp the exposed coil and move it or retrieve it from the body. The stretch-resisting member of this invention prevents the coil from stretching into a single strand of wire and multiplying in length.

Modification of the above-described variations of carrying out the invention that would be apparent to those of skill in the fields of medical device design generally, and vaso-occlusive devices specifically, are intended to be within the scope of the following claims.

I claim as my invention:

1. A vaso-occlusive device comprising:

i.) an outer helically wound primary coil having a first end and a second end, defining a lumen between said first end and second end, and ii.) a stretch-resisting member extending through said lumen and fixedly attached to said first end and second ends.

2. The device of claim 1 additionally comprising a deployment tip attached to at least one of the first end and second end.

3. The device of claim 2 wherein the deployment tip comprises a joint adapted to mechanically attach to and detach from a pusher.

4. The device of claim 2 wherein the deployment tip comprises an electrolytically detachable end adapted to detach from a pusher by imposition of a current on said pusher.

5. The device of claim 1 wherein the stretch resisting member comprises a wire.

6. The device of claim 1 wherein the stretch resisting member comprises a helical coil.

7. The device of claim 1 where the device has a secondary form.

8. The device of claim 1 comprising a metal selected from the group consisting of platinum, palladium, rhodium, gold, tungsten, and their alloys.

9. The device of claim 8 comprising an alloy of platinum and tungsten.

10. The device of claim 1 comprising an alloy selected from the group consisting of stainless steels and super-elastic alloys.

11. The device of claim 11 comprising nitinol.

12. The device of claim 1 comprising a polymer containing a radio-opaque filler.

13. The device of claim 1 additionally comprising filamentary material attached to said primary coil.

* * * * *

UNITED STATES PATENT AND TRADEMARK OFFICE
CERTIFICATE OF CORRECTION

PATENT NO. : 5,582,619

DATED : December 10, 1996

INVENTOR(S) : KEN

It is certified that error appears in the above-indentified patent and that said Letters Patent is hereby corrected as shown below:

On the title page, item [57]

*Abstract, line 13*: delete "be".

*column 1, line 19*: delete "be", second occurrence.

Signed and Sealed this

Third Day of June, 1997

Attest:

BRUCE LEHMAN

Attesting Officer

Commissioner of Patents and Trademarks